United States Patent
Vaghefi et al.

(10) Patent No.: US 7,179,407 B2
(45) Date of Patent: *Feb. 20, 2007

(54) ZERO ORDER RELEASE AND TEMPERATURE-CONTROLLED MICROCAPSULES AND PROCESS FOR THE PREPARATION THEREOF

(75) Inventors: Farid Vaghefi, Exton, PA (US); Jeffry Lee, Philadelphia, PA (US); Vijendra Nalamothu, West Chester, PA (US)

(73) Assignee: Verion Inc., Lionville, PA (US)

( * ) Notice: Subject to any disclaimer, the term of this patent is extended or adjusted under 35 U.S.C. 154(b) by 238 days.

This patent is subject to a terminal disclaimer.

(21) Appl. No.: 10/373,298

(22) Filed: Feb. 24, 2003

(65) Prior Publication Data

US 2003/0146530 A1   Aug. 7, 2003

Related U.S. Application Data

(63) Continuation of application No. 09/844,064, filed on Apr. 27, 2001, now Pat. No. 6,544,646.

(60) Provisional application No. 60/252,510, filed on Nov. 22, 2000, provisional application No. 60/199,976, filed on Apr. 27, 2000.

(51) Int. Cl.
*B01J 13/02* (2006.01)
*B32B 15/02* (2006.01)

(52) U.S. Cl. ............... 264/4.1; 264/4.32; 264/4.33; 264/4.4; 264/7; 264/9; 264/12; 264/14; 428/402.24; 428/403

(58) Field of Classification Search ............ 264/4.3, 264/4.32, 4.4, 7, 13, 4.1, 4.33, 9, 14; 428/403, 428/402.24
See application file for complete search history.

(56) References Cited

U.S. PATENT DOCUMENTS

| | | | |
|---|---|---|---|
| 5,130,171 A | | 7/1992 | Prud'Homme et al. |
| 5,204,029 A | | 4/1993 | Morgan et al. |
| 5,209,879 A | * | 5/1993 | Redding, Jr. .............. 264/23 |
| 5,246,636 A | * | 9/1993 | Lew et al. .................. 264/4.1 |
| 5,271,881 A | * | 12/1993 | Redding, Jr. .............. 264/432 |
| 6,541,030 B2 | | 4/2003 | Vaghefi |
| 2006/0104909 A1 | | 5/2006 | Vaghefi et al. |

FOREIGN PATENT DOCUMENTS

| | | |
|---|---|---|
| JP | 61242635 | 10/1986 |
| JP | 2000086502 | 3/2003 |
| JP | 62201635 | 9/2005 |

* cited by examiner

*Primary Examiner*—Stefan Staicovici
(74) *Attorney, Agent, or Firm*—Synnestvedt & Lechner LLP

(57) ABSTRACT

A microcapsule composition comprising a core material in a matrix of polymorphic shell material, releases said core material in an aqueous environment in accordance with zero order linear release profile. A preferred composition comprises a core material having a degree of water solubility entrapped in a beta crystalline matrix of water insoluble shell material which matrix may, optionally, be surrounded by a contiguous core material-free layer of water insoluble shell material. Also disclosed is a process for the preparation of microcapsules comprising subjecting a flowable mixture of core material and a first amount of water insoluble shell material to a pressure force to form a pressure-treated mixture, and passing said pressure-treated mixture through a spray nozzle into a chilling zone to form a solidified composition. A special embodiment of the method providing for the long term moisture stability of the resulting microcapsules subjects the microcapsules prepared in the first step to a second coating with a second amount of water insoluble shell material.

15 Claims, 6 Drawing Sheets

ZERO ORDER RELEASE AND TEMPERATURE-CONTROLLED MICROCAPSULES AND PROCESS FOR THE PREPARATION THEREOF

PRIOR APPLICATIONS

This application claims benefit of U.S. provisional patent application Ser. No. 60/199,976 filed Apr. 27, 2000, and U.S. provisional patent application Ser. No. 60/252,510 filed Nov. 22, 2000.

FIELD OF THE INVENTION

The present invention relates to micro-encapsulation, and more particularly to the micro-encapsulation of core materials that release the encapsulated core contents into its environment in a controlled manner. The microcapsules of the present invention are useful for example in the pharmaceutical, nutriceutical, food, cosmetics and agricultural industries.

BACKGROUND OF THE INVENTION

Microcapsules have many applications, such as in the manufacture of pharmaceuticals, herbicides, foods, cosmetics, pesticides, paints, adhesives, and many other chemical products. Microcapsules are especially useful where it is desired to provide a controlled release of the substance being encapsulated.

Various processes for forming microcapsules are described in the references: Vandegaer, "Microencapsulation Processes and Applications", Plenum Press, New York, 1974, M. Gutcho, "Microcapsules and other Capsules", Chemical Technology Review, No. 135, Noyles Data Service, Park Ridge, N.J. 1979, and the Kirk-Othmer Encyclopedia of Chemical Technology, 3rd Edition (1981), volume 15. The above-mentioned references describe several liquid-phase methods of encapsulation. These methods include coacervation, thermal coacervation, complex coacervation, interfacial polymerization, and others. In the process of coacervation, the core and shell materials are mixed together in a liquid medium. When the core and shell materials have been agitated for a sufficient period of time, portions of the core material become coated with shell material, thus forming capsules within the liquid medium. The size of these capsules is controlled by the speed and design of the mixing element within the vessel. A further chemical treatment process adjusts the thickness of the shell material.

Microcapsules used in industry must be capable of withstanding large shear forces, or other stressful conditions, when the capsules are added to a host material. Suitable host materials could be paints, plastics, foam products, building materials, paper products and others. Each host material requires varying conditions of heat and stress to produce the final product, and the capsules must have suitable physical properties to enable the capsules to be used during the manufacture of the final product. Capsules used in industry must generally be very small.

There are special problems in the development of sustained release compositions, and particularly zero order release compositions, of environmentally sensitive materials or biologically active macromolecules due to the susceptibility to chemical and structural alteration or reaction upon mixing with excipients, upon processing and upon storage. These problems are understood by those skilled in the art of pharmaceutical formulation and can be categorized as problems of chemical stability. Inadequate chemical stability of compositions resulting from irreversible alteration of the structure of the core and/or interactions with the excipients can result in compositions that are either inactive or do not provide the desired function.

Another category of problems for pharmaceutical formulations is physical stability. One obvious example is attrition of tablets or implants during processing, packaging, or storage. Another example is a physical separation of a cream, paste or gel into component parts, which can lead to a heterogeneous distribution of active ingredient as well as alteration of the consistency. The consequence of such physical deterioration of the formulation can be loss of the desired ease of use characteristics and an unpredictable dosing to the patient. Less obvious physical changes in a pharmaceutical formulation include various alterations to the crystalline or microscopic structure of the excipients. These types of changes can lead to marked alterations in the release of active agents. It should be clear that changes in the physical stability of pharmaceutical dosage forms whether they are for oral or parenteral administration would be most problematic for sustained release preparations. It is the sine qua non of commercially viable sustained release pharmaceutical dosage forms that they have maintained release characteristics across production lots and after relatively long periods of time in storage. Physical stability of the pharmaceutical dosage form is intended to describe both constancy of the handling characteristics such as hardness, flowability, or viscosity, and constancy of pharmacological performance.

The present invention provides a specific dual mechanism release profile microcapsule and a method for its preparation.

Reported Developments

Microencapsulation technology has long been used for the controlled delivery of pharmaceuticals. As early as 1964 aspirin was encapsulated in ethylcellulose (U.S. Pat. No. 3,155,590) with improvements made to the basic process (U.S. Pat. No. 3,341,416). Microencapsulation has also been used to deliver potassium salts to humans (U.S. Pat. No. 4,259,315).

Other drugs have also been microencapsulated using a variety of methods. For example, U.S. Pat. No. 4,938,967 discloses microcapsules with a higher than usual density by including a weighting agent, such as barium sulphate, to increase the residence time in the stomach. U.S. Pat. No. 4,574,080 discloses a controlled release formulation that contains additional particles of the active substance adhered to the surface of the coating. U.S. Pat. No. 4,606,940 discloses a process for encapsulation by dissolving the compound to be encapsulated in a solvent, mixing the solution with a solution of encapsulating material and electrolyte, and gelling the encapsulating material.

One of the primary reasons for encapsulating a drug is to slow the release of the drug into the body. Thus, a controlled release microencapsulated formula may be substituted for several non-microencapsulated doses. The release rate of the drug is typically controlled primarily through the thickness of the coating. Typically the release pattern is first order in which the rate decreases exponentially with time until the drug is exhausted (Kirk-Othmer, Encyclopedia of Chemical Technology, p. 485, 1981). This release pattern is due to the concentration difference between that inside and that outside the capsule which difference decreases continuously during dissolution.

Exemplary sustained release microcapsules include those described in the following patents:

U.S. Pat. No. 4,837,381 discloses a microsphere composition of fat or wax or mixture thereof and a biologically active protein, peptide or polypeptide suitable for parenteral administration. The patent discloses the utility of the compositions for slow release of a protein, peptide or polypeptide in a parenteral administration, and discloses methods for increasing and maintaining increased levels of growth hormone in the blood of treated animals for extended periods of time and thereby increasing weight gains in animals and increasing milk production of lactating animals by the administration of compositions of the invention.

U.S. Pat. No. 5,213,810 discloses water insoluble fat or wax microspheres containing biologically active protein, peptides or polypeptides wherein the fat or wax shell includes an oil, semi-soft fat or fatty acid derivative disclosed as stabilizing the microsphere by accelerating the formation of the beta crystal form of the fat or wax subsequent to spray atomization of the mixture.

However, often a zero order, constant-release rate is preferred in which case the microcapsules deliver a fixed amount of drug per unit time over the period of their effectiveness. Zero-order release core delivery systems provide for the core to be released at a uniform rate independent of the core concentration (in the dosage form) during the period of release. Such an ideal core delivery system can produce uniform core concentration levels for a prolonged period of time. In a pharmaceutical system, the zero-order delivery system is capable of providing maximum therapeutic value while minimizing the side effects. It-can also reduce the dosing frequency to once in twelve hours or once in twenty-four hours, thus improving the dosage compliance on the part of subjects.

Except for reservoir devices, zero-order release of microcapsules has rarely been reported. Zero-order release with reservoir devices is obtained until no excess drug is left in contact with a saturated drug solution in the reservoir. For example, in the 1986 paper, M. Donbrow, School of Pharmacy, Jerusalem, Israel presented at the 13th International Symposium on Controlled-Release of Bioactive Materials, Aug. 3–6, 1986—Norfolk, Va., the author states "Microcapsule release literature includes many unvalidated reports of exponential release, also some matrix release ($M = kt^{1/2}$ or Higuchi kinetics), and dissolution rate-limiting release ($m^{1/3}$ alpha. t), but very rarely zero-order release."

A pertinent recent purported example of a zero order release microcapsule composition is reported in U.S. Pat. No. 5,252,337, which discloses an ethylcellulose microcapsulated formulation of a calcium channel blocker with a controlled release from about 8 to about 24 hours, more narrowly from about 12 to about 16 hours. The '337 patent discloses that the ethylcellulose microencapsulated formulation of a calcium channel blocker exhibits an approximately zero order release rate.

U.S. Pat. No. 3,845,770 describes an osmotic device for the zero-order release of an active agent. The osmotic device disclosed in this patent consists of an active agent enclosed in a semi-permeable wall. The semi-permeable wall is permeable to the passage of an external fluid but is substantially impermeable to the passage of the active agent in solution with the external fluid. An osmotic passageway is provided through the wall to deliver the solution of the active agent in the external fluid to the environment. The patent thus teaches the use of osmotic delivery of the active agent solution through a specially constructed passageway instead of delivery via diffusion through a membrane.

U.S. Pat. No. 4,327,725 describes how to enhance the delivery kinetics of the basic osmotic pump via use of a hydrogel layer inside the semi-permeable membrane. The structure of the device consists of an active agent enclosed in a hydrogel layer that is enclosed by a semi-permeable membrane. The semi-permeable membrane allows diffusion of external fluid to inside but does not allow the diffusion of the solution of active agent in the external fluid to the surrounding environment. The hydrogel swells with absorption of external fluid and exerts pressure on the solution of active agent in the external fluid. The solution of the active agent in the external fluid is then delivered to the surrounding media through a single specially constructed passageway through the hydrogel layer and the membrane. It is claimed that the variation described in U.S. Pat. No. 4,327,725 is particularly useful in case of drugs that are insoluble in the external fluid. The osmotic passageway in the device described in this patent is created by drilling a hole through the semi-permeable wall to connect the active agent compartment with the exterior of the device. A laser-machine is utilized to drill precise holes. This procedure is cumbersome and requires a considerable development effort to tailor the delivery system to each individual drug or active agent.

U.S. Pat. No. 4,891,223 discloses a bioactive composition having a controlled, sustained release delivery pattern when contacted with a suitable surrounding media. The composition comprises a pharmaceutically, insecticidally, herbicidally or fertilizing bioactive material core, soluble in a given surrounding media, the core present in an amount at least sufficient for a total dosage during a treatment period; a first coating enveloping the bioactive material core comprising a polymer or a blend of polymers, said polymer or blend of polymers being swellable upon penetration by the surrounding media; and a second coating enveloping the first coating enveloped bioactive material core comprising a polymer or a blend of polymers; said polymer or blend of polymers being water-insoluble and forming a semi-permeable barrier permitting diffusion of the surrounding media into the first coating enveloped bioactive material core and also permitting the diffusion of the surrounding media dissolved bioactive material into the surrounding media. The first coating can further comprise a plasticizing agent. Examples of suitable first coating polymers are hydroxypropyl cellulose, hydroxypropyl methyl cellulose, polyvinyl alcohol or mixtures thereof Examples of suitable second coating polymers are ethyl cellulose alone or in combination with hydroxypropyl cellulose or methyl cellulose.

Similar internally swellable microcapsule compositions are disclosed in the following patents:

U.S. Pat. No. 4,423,099 discloses non-uniform water-insoluble interpenetrating polymer blend compositions comprising a first permeable water swellable polymer substrate interpenetrated in a gradient substantially normal to the substrate surface by a second less permeable condensation polymer to form a diffusion rate controlling membrane therein. The resulting polymer blend is such that the concentration of the condensation polymer increases from 0% at the inner surface of the water swellable polymer to about 100% at the outer surface of the water swellable polymer.

U.S. Pat. No. 4,177,056 discloses a controlled, sustained release composition comprising a pharmaceutically, insecticidally or herbicidally effective agent and a water-insoluble hydrophilic gel comprising: (A) about 30 to about 90% of a hydrophilic (a) polymer of identical or different water-soluble mono-olefinic monomers, or (b) copolymer of the water-soluble monomers with 1 to 70% of water-insoluble, identical or different mono-olefinic monomers, which polymer or copolymer is cross linked with (B) about 10 to about 70% of a terminal diolefinac hydrophobic macromer having a molecular weight from about 400 to about 8000.

U.S. Pat. No. 4,138,475 discloses a sustained release pharmaceutical composition consisting of a hard gelatin capsule containing film-coated spheroids, comprising propranolol or a pharmaceutically acceptable salt thereof, in admixture with a non-water swellable microcrystalline cellulose, with the spheroids having a film coat comprising ethylcellulose optionally together with hydroxypropyl methylcellulose and/or a plasticizer.

The food, nutriceutical, cosmetic and agricultural industry have benefited from the use of microcapsules prepared from encapsulating core materials in either hydrophilic or hydrophobic polymeric materials. These microcapsules have been prepared from molten mixtures which are both cooled and granulated or spray chilled thereby congealing the molten polymer about the core materials to form capsules or prills.

U.S. Pat. No. 5,599,583 discloses the encapsulation of an agriculturally effective active ingredient by mixing until homogeneous the ingredient with a water-free molten film-forming water soluble polymer binder, cooling the mixture and spraying the cooled mixture into a congealing zone to form particles.

U.S. Pat. No. 5,631,013 discloses encapsulated alkali metal bicarbonate crystallites coated with hydrophilic or water insoluble polymers, and specifically describes the fluicized bed coating of sodium bicarbonate using solutions of hydrophilic polymers.

U.S. Pat. No. 3,080,293 discloses the preparation of niacinamide beadlets by admixing melted stearic acid with niacinamide powder passed through a centrifugal atomizer and spray chilled, dried and dusted with silicic acid.

U.S. Pat. No. 4,022,917 describes a batter that is made with particles of an alkaline leavening agent encapsulated in a water-insoluble coating that is added to the batter. The alkaline leavening agent is dispersed in the batter at a cooking temperature and is released at a temperature of at least about 60 degrees C.

The use of fats as a retention media for volatiles is disclosed in U.S. Pat. No. 3,949,094, wherein volatile flavorings, seasonings, colorants, flavor enhancers and the like are blended with lipoid material under super atmospheric conditions for subsequent handling or conversion into particulates by a spray chilling process. The '094 patent method and other similar spray-drying methods result in microcapsules of inferior quality. In essence, the "sealing" effect of core materials within fats by prior art methods is often insufficient resulting in unwanted core oxidation, reduction or volatilization, particularly when the capsules are exposed to environmental storage conditions or mechanical shear during subsequent processing.

More recent methods of microencapsulation are reported in U.S. Pat. No. 5,209,879 which discloses the use of a pressure-pulse, abrupt pressure change or shock wave (hereinafter "pressure-force") to accelerate the conversion of polymorphic waxes to the more stable beta crystalline state and the use of such beta waxes as shell materials in the preparation of microcapsules for environmentally sensitive materials. WO9115198, derived from a US application filed on the same day as the application that issued as the above-mentioned '879 patent, discloses the possible preparation of a beta crystalline wax encapsulate by the pre-mixing of the core material with the liquid wax prior to the application of the pressure-force. The patentee notes however that this procedure results in frequent machine jamming. The pressure pulse technology has also been described as applicable to the encapsulation of fluids such as liquids in U.S. Pat. No. 5,460,756 that discloses the encapsulation of liquids within the pressure force-treated polymorphic wax by mixing the liquid core with the molten wax either before or after subjecting the mixture to pressure force. In all the pressure force methods, the molten mixture is cooled and granulated to form the stabilized beta wax encapsulated microcapsules.

It is an object of this invention to provide long term storage-stable microcapsule compositions that possess the capacity to release core material at a constant rate in an aqueous environment and/or release the core as a function of a defined temperature range. These and other objects will become apparent in the following description of the invention.

SUMMARY OF THE INVENTION

The present invention relates to a microcapsule composition comprising a core material in a matrix of polymorphic shell material, where, in an aqueous environment, said core material is released from said microcapsule in accordance with zero order linear release profile. A preferred composition comprises a core material entrapped in a beta crystalline matrix of water insoluble shell material which matrix may, optionally, be surrounded by a contiguous core material-free layer of water insoluble shell material.

The present invention relates also to a process for the preparation of microcapsules comprising subjecting a flowable mixture of core material and a first amount of water insoluble shell material to a pressure force to form a pressure-treated mixture, and passing said pressure-treated mixture through a spray nozzle into a chilling zone to form a solidified composition. A special embodiment of the method providing for the long term moisture stability of the resulting microcapsules subjects the microcapsules prepared in the first step to a second coating with a second amount of water insoluble shell material.

DETAILED DESCRIPTION

Figure 1:
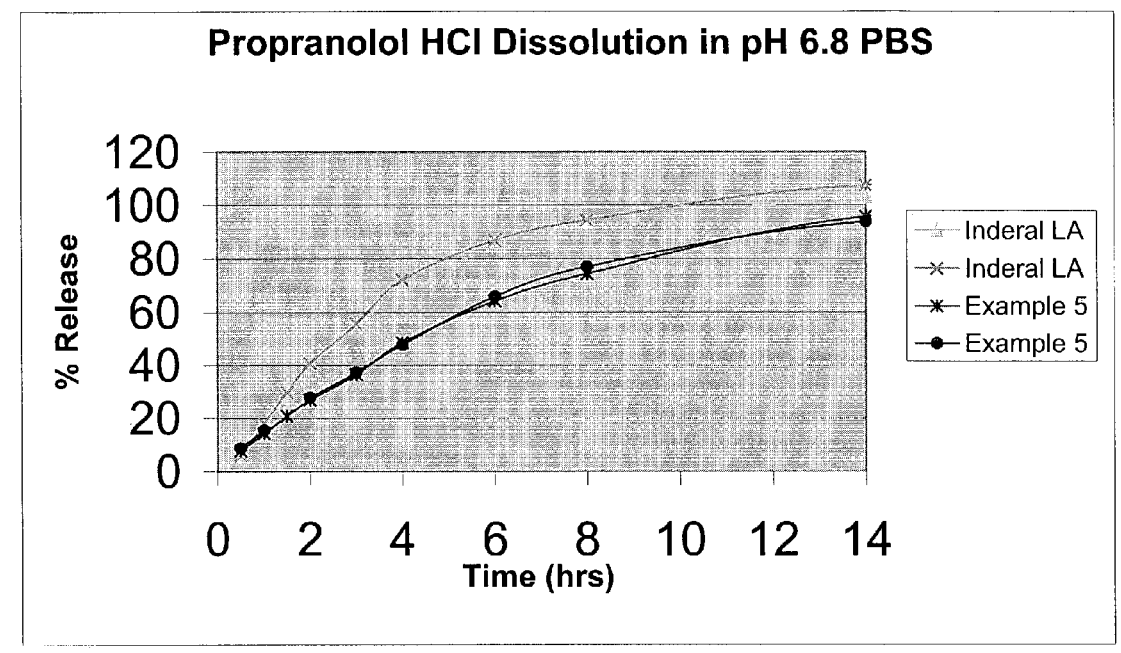
FIG. 1 is a plot of the percent release versus time data for the microcapsule of Example 5 in comparison to the dissolution profile of a commercially available long acting propranolol-containing product.

The compositions of the present invention provide a highly stable and protective carrier vehicle for the core material, until activated to release the core material by means of one or more mechanisms including a temperature release mechanism that permits core release over a pre-defined temperature range and a dissolution mechanism that permits the zero order release of the core material over a predetermined period of time in an aqueous environment.

The term "zero order release" or "zero-order release rate" as used herein means a constant, linear, continuous, sustained and controlled release rate of the core material from the microcapsule, i.e. the plot of mass of core released vs. time is linear.

The term "capsules" or "encapsulated particles" as used herein refers to particles that have a shell component and a core component wherein the shell component encloses the core component, which may be a single core or comprise numerous cores dispersed among the shell material as a matrix.

The term "microcapsule" as used herein is a capsule that has a diameter of the order of about 5–5000 microns.

The core material may be a liquid droplet, a solid particle, a gas, or slurry composed of a solid and liquid mixture. Any material that retains its shape and configuration, within the liquid medium, can be used. The core material may be soluble or insoluble within the liquid medium. Preferred materials are insoluble, or only slightly soluble at processing conditions, in the shell material.

The shell material is a water insoluble organic material, and preferably is a naturally derived or synthetically produced wax material, which may comprise a single chemical component or a mixture thereof. The shell material is most preferably a triglyceride or a mixture of triglycerides such as is found in hydrogenated or partially hydrogenated vegetable oils.

The term "wax" as used herein is intended to have as broad a meaning as possible and contemplates organic ester and waxy compounds derived from animal, vegetable, and mineral sources including modifications of such compounds from all three sources in addition to synthetically produced materials having similar properties. Examples of some of the waxes that may be used either alone or in combination with this invention are shown below in Table 1.

TABLE 1

| | |
|---|---|
| glyceryl tristearate | glyceryl distearate |
| Dynasan ™ 110, 114, 116, 118 | Sterotex ™ Hm, k |
| canola wax/oil | cotton flakes |
| soya flakes | castor wax |
| rapeseed wax | beeswax |
| carnauba wax | candelilla wax |
| microwax (petroleum boler ™ Wax 1014 based) | Dritex C ™ |
| special fat ™ 42, 44, 168 t | Be Square ™ Wax #195a |
| Be Square ™ Wax #195w | Energybooster ™ |
| Astor ™ Wax 180 | Astor ™ Wax 150 |
| polyethylene | meltable polymers |

The commonly used class of waxes useful in the present invention are known as the triglycerides. In nature, triglycerides are usually found in complex mixtures. Depending upon the source of the triglyceride, whether animal or plant, the triglyceride may be formed from shorter or longer carboxylic acids which may in turn be either saturated or unsaturated. Triglycerides formed from shorter chain, unsaturated carboxylic acids, as a rule, melt at a lower temperature than triglycerides formed from longer-chain, saturated acids. In most cases, triglycerides are formed of more than one type of carboxylic acid. Further, the physical characteristics of a triglyceride (such as whether it exists as a liquid or solid at room temperature) are determined not only by which carboxylic acids were incorporated by esterifcation but also in which of the glyceryl hydroxy positions a given carboxylic acid was incorporated. Thus, animal triglycerides differ from plant triglycerides not so much in the overall ratios of saturated to unsaturated acids or of acids of given lengths, but rather in which of the three hydroxy positions in the glyceryl molecule unsaturated acids are to be found. Also, typically, naturally occurring triglyceride waxes, which are solid at room temperature, do not display a single sharp melting point because of the wide range of triglycerides present in most natural products.

Triglyceride waxes may be obtained commercially with a choice of chain length of the carboxylic acids that form the triglycerides, as well as a choice of purity grades. Commercial preparations of triglycerides start with natural products in which a number of different triglycerides are associated with each other. Processing not only saturates the acid substituents but also reduces the variety of triglycerides in the final material. The method and apparatus of this invention may be clearly demonstrated using the monoacid triglyceride, glyceryl tristearate ("tristearin") formed by the esterification of 18-carbon stearic acids with all three hydroxy groups of glyceryl. Stearic acid is a fully saturated carboxylic acid. One suitable commercial grade of tristearin of which Applicant is aware is a product having the trademark "Dynasan™ 118" which is manufactured by Dynamit Nobel, a subsidiary of Hulls America. Dynasan™ 118 is a highly purified material from a vegetable source that contains relatively few triglyceride molecules that have esterified acids of different lengths. Similar, although somewhat less pure triglyceride materials are also commercially available under the trademark Sterotex™. As it is supplied by the manufacturer, Dynasan 118 is a white microcrystalline powder crystallized in the beta form, the DSC of which exhibits a single endothermic peak centered at approximately 72. degree. C. indicating that only a single polymorphic form is present with a melting point within the melting point temperature range of the beta form. Other preferred triglyceride waxes include Dritex C, a hydrogenated cottonseed oil wax, and BF117 (Bakers Flake 117) now sold as Shurset 117, partially hydrogenated soybean oil, both of which are sold commercially by AC Humko.

"Beta crystals" and "fat in a beta form" as used herein refer to triglyceride crystals having a blocky symmetry, and a length of about 50–100 microns on a side. Beta crystals of triglycerides are aligned in parallel rows. A presence of beta crystals may be determined by a method such as differential scanning calorimetry (DSC) as described in the AOCS Recommended Practice Cj 1-94. The presence may also be determined by x-ray diffraction analysis using a method such as is described in AOCS Cj 2-95 and by low-resolution nuclear magnetic resonance using AOCS method Cd 16b-93.

The process of the present invention comprises applying a pressure force to a mixture of core and shell materials, for a short time, of the order of one second or less, followed by atomizing or spraying the molten mixture into a chilling zone to congeal the molten shell material around the core material. The mixture of core and shell materials, before a pressure force is applied, is referred to hereinbelow as the "pre-mixture". A preferred process adapted to prepare storage stable compositions comprising water soluble inorganic core materials applies a second outer layer of shell material free of core material to the shell coated core material. The shell material may be applied as an outer layer with any of the typical coating methods known in the prior art but the most preferred process applies the shell material by means of spray coating.

The pressure force is applied to the pre-mixture in accordance with the method and apparatus (Beta apparatus) described in U.S. Pat. No. 5,209,879, which is hereby incorporated by reference.

The compressive forces are generated by compacting the pre-mixture during a short time interval and forcing the compacted pre-mixture through the "beta" chamber thereby subjecting the mixture to a shear and cavitation forces resulting from the high-pressure surges and currents created in a post pressure reduction chamber. This process is described in U.S. Pat. Nos. 4,978,483, 5,460,756, and 5,209,879 all hereby incorporated by reference. These forces are believed to micronize the core materials and compress the shell material intimately about, and into the imperfections of, the core surfaces.

The amount of pressure force required, in the present invention, depends on the time interval during which the pressure is applied. The required pressure varies inversely with that time interval. The coating process continues as long as the pressure is maintained on the pre-mixture, but the coating is most effective when the pressure is applied for a very short period of time, preferably on the order of one second or less. To amplify the effectiveness of the pressure force processing, the pressure-treated mixture may be repeatedly subjected to the application of pressure in the Beta apparatus. The flowable composition may be passed through the Beta apparatus one, two or even three times to achieve the desired effect.

The core material may be a solid, liquid, gas or slurry. As a result of the application of pressure force, the shell material surrounds and encapsulates any particle, or gas or liquid droplet, which is present within the pre-mixture. If the core material is a solid, the shell material will generally coat the particle easily as the pressure shock wave surrounds the particle with shell material. Eventually, under pressure, the shell material forms a complete enclosure of the solid particle, and solidifies as a contiguous layer, thereby forming an encapsulated solid.

If the core material is a liquid droplet, the liquid core material must have a viscosity that differs from that of the liquid medium in which it is immersed. If the viscosity of the liquid core is too close to that of the liquid medium, the shell material, when compressed, tends to displace the liquid droplet and forms globular spheres composed solely of the shell material. The liquid droplet then dissolves and disperses within the liquid medium, and tends not to become encapsulated. The core material is preferably a liquid droplet that is not soluble in the shell material. If this is so, the pressure force will tend to form the shell material into an encapsulating coating around the liquid core droplet. The shell material then solidifies and seals the droplet, forming an encapsulated liquid.

If the core material is soluble within the liquid medium, the preparation of the pre-mixture and the application of the pressure-force prior to salvation of the core into the shell material are required to enable the encapsulation to take place.

If the core is a gas bubble within the pre-mixture, then the pressure-force will "recognize" the bubble as a solid form and will enclose the bubble with the shell material, thereby forming a gas-filled microcapsule.

The present invention improves upon the prior art microencapsulation processes in several ways including the manner in which the pressure-treated mixture is formed into microcapsules. While the prior art uses either a solvent system and separates the solvent insoluble microcapsules from the pressure-treated stream, or slowly cools the pressure-treated molten mass while granulating, the present invention incorporates a second step comprising atomizing or spray chilling the flowable pressure-treated pre-mixture to form the microcapsules.

This combination technique thus includes two steps, namely a molten-phase stage, wherein pre-formed capsules are made in a molten mass subject to a pressure pulse, and a spray chilling stage, which completes the encapsulation process. The spray chilling stage involves the passing of said pressure-treated mixture through a spray nozzle into a chilling zone to form a solidified composition; wherein said zone is at a temperature below the solidification temperature of said shell material. The temperature of the pressure treated mixture as it transits through the pressure-pulse apparatus and until it reaches the spray nozzle should be maintained below the melting temperature of said shell material but above its solidification temperature. The temperature of the spraying, the configuration of the spray nozzle, and the flow rate through the nozzle all influence the physical characteristics of the resulting microcapsules. A most preferred process uses a heated spray nozzle (and heated tubings and conduits leading up to said nozzle) that ensures that the pressure-treated mixture maintains a viscosity suitable for a high spray throughput. Such high throughput enables the formation of substantially spherical microcapsules upon cooling the sprayed particles of liquid mixture below the solidification temperature of the shell material.

The shell material most preferably exhibits a melting curve where melting begins at T1 and is substantially complete at T2, and exhibits a cooling curve where solidification begins at T3 and is substantially complete at T4, wherein T3 is less than T1. The difference between T1 and T2 for any particular shell material used in the present method is determined by the ratio of wax materials comprising said shell material. By modifying the ratio of components in the shell material, the temperature characteristics, and hence release characteristics, of the microcapsules produced by the present method, may be predetermined. Furthermore, by determining the melting and solidification temperatures for the particular shell material used in the present method, the temperatures of the mixture during treatment may be adjusted accordingly to avoid jamming or clogging of the apparatus during operation.

The application of a pressure pulse to the pre-mixture accelerates the solidification of the resultant microcapsule shell material into the beta crystalline form of the polymorphic wax or mixture of polymorphic waxes comprising the shell. Consequently, the resulting microcapsules are stable, lacking the majority of the fissures and cracks appearing in microcapsules prepared using a one step process, that is the methods taught by the prior art. Furthermore, the resulting microcapsules are protected from the environment to a degree not possible with the prior art methods.

Microcapsules formed from the process according to the present invention are range in size from about 50 to about 900 microns in size, and may have a variety of shapes including spherical, elongated or even rod-like. The preferred microcapsules are substantially spherical in shape, and have an average particle size of between about 150 to about 800 microns. A microcapsule having an average particle size of about 50 to about 500 microns preferably includes a solid core material having an average particle size of about 10 to about 300 microns. Depending on the application, preferred microcapsules have an average particle size of 50 to 250 microns include solid core particles having an average particle size of about 10 to about 50 microns. In other applications, the more preferred microcapsules have an average particle size of about 300 microns to about 500 microns, and most preferably from about 300 to about 450 microns.

The release properties of the microcapsules prepared using the aforesaid two-step process is a function of the percentage of core in the microcapsule composition, the ionic nature of the core material, the size and shape of the microcapsule, and the shell composition. Where a microcapsule includes an inorganic water soluble core compound, such as an inorganic salt, furthering processing may be required to achieve a long term linear release profile.

In a special embodiment of the present invention, the microcapsules formed in the two-stage method are contacted with a second amount of a water insoluble shell material to form an outer coating of shell material. The outer layer of water insoluble shell is substantially free of core material and surrounds the encapsulated core material in a contiguous layer. In this embodiment of the invention, the outer contiguous layer is formed by spray coating onto the microcapsules a composition comprising from about 5 to about 30 percent by weight of the first amount of shell material. A more preferred second amount of water insoluble shell material is about 10 percent by weight of said first amount of shell material.

The second amount of shell material may be any water insoluble organic material typically used in the encapsulation arts. A preferred second shell material comprises one of the waxes described herein, and a preferred embodiment utilizes the same polymorphic shell material composition of the first amount used in the method of the present invention. It is believed that the use of the same polymorphic material for both encapsulating operations results in an extremely stable structure due to the seeding of the outer polymorphic layer with the pressure "forced" beta crystals of the inner shell. As a consequence of the inner shell seeding effect, the microcapsule of the present invention exhibits unexpected stability and long-term zero-order core release properties in aqueous media.

The zero order core release rate is believed to occur due to the slow erosion of minute imperfections in the microcapsules of the present invention which form "tortuous" paths throughout the matrix of the inner encapsulate thereby providing ingress of aqueous media and egress of solubilized core. Unlike the prior art compositions, the shell materials are not swellable and do not rely on osmotic pressure to release core materials.

In one preferred embodiment, the microcapsules have a core content in a range of about 10 to about 45% by weight, preferably about 20 to about 35% by weight.

In another embodiment of the invention, the core material comprises a water soluble organic compound, which may preferably be an salt of an organic acid or base. Microcapsule compositions including such organic salts and prepared according to the present process are capable of linear release in an aqueous environment of about 50 to about 100 percent of the core material over a period of about 8 to about 24 hours. Preferred microcapsules of the present invention are capable of linear release of about 70 to about 100 percent of the core material over a period of about 10 to about 14 hours, and most preferably about 12 hours. Another preferred composition is capable of linear release of about 80 to about 100 percent of the core material over a period of about 20 to about 26 hours, preferably about 22 to about 25 hours, and most preferably about 24 hours.

Preferred organic compound salts include pharmaceutically acceptable salts, such as mineral acid salts such as hydrogen halide acid salts such as hydrochloric acid salts, and phosphoric acid and sulfuric acid salts. Another class of preferred salts are the organic acid salts of organic bases, including the pharmaceutically acceptable carboxylic acids such as citric acid, tartaric acid, acetic acid, maleic acid, estoleic acid, succinic acid and the like:

In another embodiment of this invention, microcapsules include core materials that are water insoluble or slightly water soluble organic compounds. A linear release profile may be achieved with such core materials provided the shell material comprises a mixture of materials including a polymorphic wax material with a second material that increases the polar nature of the shell matrix. It is believed that by increasing the polar nature of the shell matrix the core material may be more easily solvated by the aqueous media and hence result in faster core material release. Exemplary polar materials include fatty acids or fatty alcohols, such as stearic acid, palmitic acid, stearyl alcohol, or cetyl alcohol, as well as polysaccharides, such as xanthan gum. The polar material may be incorporated into the shell mixture in an amount of about 10 to about 50 percent.

The water insoluble organic core material may include a functional group capable of protonation under certain pH conditions. Such materials tend to release faster in the microcapsules of the present invention the under neutral to acidic conditions, such as in the stomach and large intestine, the more acidic the environment, the faster the release. Similarly, water insoluble organic core materials capable of donating a proton and thereby becoming negatively charged, such as compounds including carboxylic acid functionality, tend to release faster under slightly basic to basic conditions, such as in the small intestine. In either case, the incorporation into the shell mixture of a polar component enhances the ability of the water insoluble or slightly water soluble organic core compound to be released in a linear manner over a time from about 8 to about 24 hours, more preferably from about 10 to about 24 hours and most preferably from about 12 to about 24 hours.

Another aspect of this invention relates the formulation of the microcapsule compostions including water insoluble or slightly water soluble organic core compounds, and comprises the admixture of an micronized inorganic salt or surfactant with said core material. The micronized salt or surfactant may be incorporated into the pre-mixture in amounts of from about 0.5 to about 10 weight percent of based on said core material, and may be used in combination with the use of a polar shell material, or independent of said polar material.

Depending on the environmental conditions to which the present microcapsules are subjected, the minor cracks or fissures may widen and accelerate core release. The present microcapsules are capable of being designed to respond to such conditions to achieve a desired release effect. For example, the shell material composition may be designed to melt between a specified temperature range, thereby releasing the core material suddenly or over a period of seconds, to minutes to an hour or more. The microcapsule is capable of being designed to release its core slowly at or about human or animal body temperature, or as a function of ambient temperature, for example on days where the air temperature rises above a set point such as 100 degrees F. Such temperature sensitive microcapsules are useful in baking applications, agricultural applications, and pharmaceutical or cosmetic applications.

The following example demonstrates the practice of the present invention in the preparation of an encapsulated sodium bicarbonate useful in the formulation of moisture stable bakery product applications.

Example 1

Encapsulated Sodium Bicarbonate (20/80 Shell)

780 g of Dritex C and 3.12 kg of BF117, commercially available polymorphic waxes are mixed together and melted. Milled sodium bicarbonate (<10 micron particle size) is mixed into the melted wax mixture, which is then subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at 140 degrees F at a pump pressure of 15 psi, aspirator pressure of 40 psi, needle set at 1.5 turn open from closed, into a chilled area. The spray-chilled sample is introduced into a Glatt brand air spraying column and spray coated with the same wax mixture until the weight percentage of the total wax content reached 70%.

The microcapsule prepared according to Example 1 is capable of releasing its core bicarbonate by two mechanisms, temperature and aqueous infiltration. The shell mixture used in Example 1 melts over a temperature range of about 106 degrees F. to about 135 degrees F. and releases bicarbonate over this temperature range. Furthermore, the Example 1 microcapsule exhibits a zero order release profile when introduced into an aqueous environment. The release of sodium bicarbonate occurs at a constant rate until 90% of the bicarbonate is released after more than 10000 minutes of stirring at room temperature. The bicarbonate release was measured using a titration method. The percent release versus time data is presented below in Table 2.

TABLE 2

Two Samples Microencapsulated Bicarbonate/
% Bicarbonate Released In Aqueous Medium over Time

| Time (min) | Percent bicarb free | Time (min) | Percent bicarb free |
|---|---|---|---|
| 1 | 1.68 | 3 | 1.96 |
| 68 | 2.24 | 70 | 2.8 |
| 174 | 2.97 | 175 | 3.36 |
| 240 | 3.5 | 240 | 4.2 |
| 399 | 4.92 | 400 | 5.04 |
| 541 | 6.04 | 542 | 5.88 |
| 1446 | 15.4 | 1449 | 15.12 |
| 1621 | 17.53 | 1623 | 16.18 |
| 3098 | 25.37 | 3100 | 24.3 |
| 3417 | 27.77 | 3419 | 27.1 |
| 5085 | 40.66 | 5085 | 43.35 |
| 7293 | 65.58 | 7293 | 63.95 |
| 7735 | 70.62 | 7735 | 70.12 |
| 10190 | 87.42 | 10190 | 89.72 |

Example 2

Encapsulated Sodium Bicarbonate (30/70 Shell)

The procedure of Example 1 was used except that a 30/70 mixture of Dritex C and BF117 was substituted for the shell material.

The shell mixture used in Example 2 melts over a temperature range of about 107 degrees F. to about 140 degrees F. and releases bicarbonate over this temperature range. The Example 2 microcapsule also exhibits a zero order release profile when introduced into an aqueous environment although releases the core bicarbonate at a slightly faster rate. The release of sodium bicarbonate occurs at a constant rate until 90% of the bicarbonate is released after more than about 7200 minutes of stirring at room temperature. The bicarbonate release was measured using the same titration method as used in Example 1.

By adjusting the mixture of waxes in the shell material, the microcapsules of the present invention are capable of being designed to release its core material at a preselected temperature as well as at a constant rate over a predefined specified period of time.

Comparative Example 3

Encapsulated Sodium Bicarbonate (20/80 Shell-Uncoated)

The procedure and materials of Example 1 were used to prepared microcapsules except that the spray coating was not applied to the microcapsules after the formation with the hot melt applicator. The microcapsules included 70% by weight of the shell composition (20/80 component mixture).

The aqueous release profile was non-linear releasing 20% bicarbonate in less than one minute, about 30% in about 21 minutes, 45% in about 273 minutes, 55% in about 395 minutes, 80% in about 1313 minutes, about 90% in about 2803 minutes and more than 93% in about 4332 minutes.

Comparative Example 4

Prior Art Granulation of Sodium Bicarbonate

Milled sodium bicarbonate (<10 microns) is mixed with BF117 while heating the BF117 into a molten state. The molten mixture is cooled and granulated. The resulting microcapsules contained 40% by weight of sodium bicarbonate and 60% BF117 shell material.

The microcapsules of Example 4 exhibit a non-linear release of bicarbonate in the aqueous environment of the release testing method described herein. The microcapsules released about 16% bicarbonate in about 1.6 minutes, about 27% in about 10 minutes, about 30% in about 16 minutes, about 41% in about 56 minutes, about 57% in about 161 minutes, about 69% in about 285 minutes, about 78% in about 407 minutes and more than 98% in about 1324 minutes.

Example 5

Zero-Order Release Propranolol HCl Composition 428 g of milled propranolol HCl (<10 micron particle size) is mixed into a melt of 800 g of Dritex C, a commercially available polymorphic wax. The flowable pre-mixture is then subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at 77 degrees C, driven by an electronic gear pump (Nordson 3700 series, speed setting=40%), aspirator pressure of 10 psi, needle set at ⅞ of a turn open from closed, into a chilled area. The propranolol HCl comprises 34.9% by weight of the microcapsule composition.

The microcapsule prepared according to Example 5 is capable of releasing its core propranolol by aqueous infiltration and exhibits a zero order release profile when introduced into an aqueous environment. The release of propranolol (−20+40 mesh fraction) occurs at a constant rate for about 14 hours of stirring in a dissolution basket at 50 rpm at 37 degrees C. in accordance with the USP Test 2 method (as modified, 900 ml of 0.05M phosphate buffer, pH 6.8). The percent release versus time data for the microcapsule of Example 5 in comparison to the dissolution profile of the commercially available long acting propranolol-containing product sold under the mark "Inderal LA" is presented in FIG. 1.

Example 6

Zero Order Release of Propranolol HCl Microcapsules 472.5 g of milled propranolol HCl (<10 micron particle size) is mixed into a melt of a mixture of 975 g of carnuba wax and 52.5 g of xanthan gum. The flowable pre-mixture is then subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at 77 degrees C., driven by an electronic gear pump (Nordson 3700 series, speed setting=50%), aspirator pressure of 10 psi, needle set at 1.5 turn open from closed, into a chilled area. The propranolol HCl comprises 31.5% by weight of the microcapsule composition.

Figure 2:
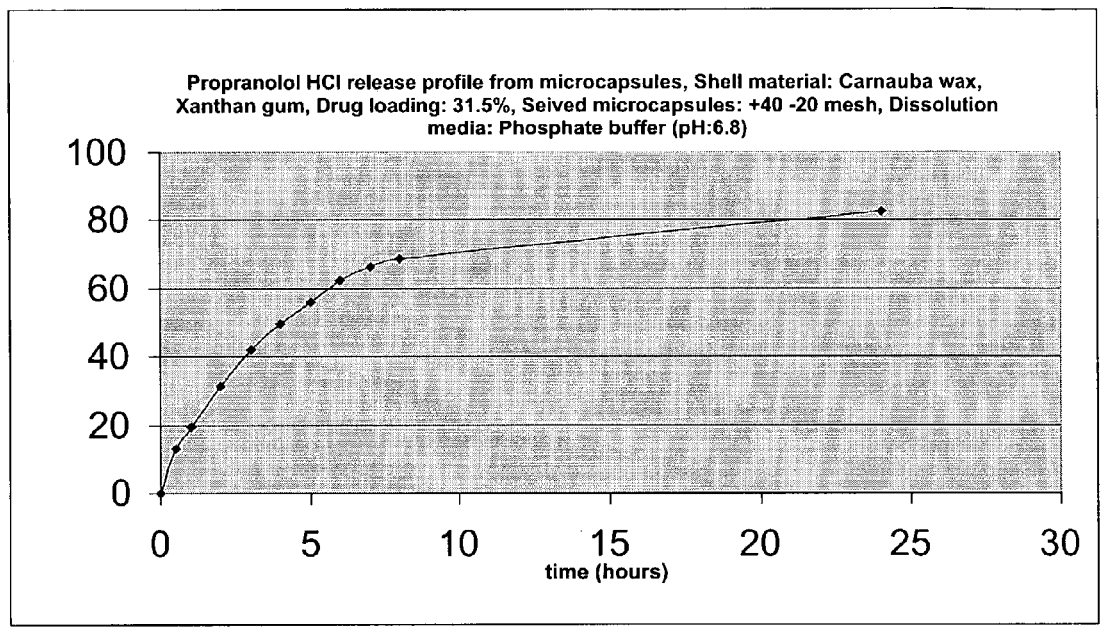
FIG. 2 is a plot of the release of propranolol (−20+40 mesh fraction) composition of the present invention versus time.

The microcapsule prepared according to Example 6 is capable of releasing its core propranolol by aqueous infiltration and exhibits a zero order release profile when introduced into an aqueous environment. The release of propranolol (−20+40 mesh fraction) reaches about 70% at a constant rate for about 8 hours of stirring in a dissolution basket at 50 rpm at 37 degrees C. in accordance with the USP Test 2 method (as modified, 900 ml of 0.05M phosphate buffer, pH 6.8). The percent release versus time data is presented in FIG. 2.

Example 7

Zero-Order Release Diltiazem HCl Composition 268 g of unmilled diltiazem HCl is mixed into a melt of 520 g of Dritex C, a commercially available polymorphic wax. The flowable pre-mixture is then subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at 77 degrees C. at a pump speed of 30%, aspirator pressure of 10 psi, needle set at 1.5 turn open from closed, into a chilled area. The diltiazem HCl comprises 34% by weight of the microcapsule composition.

Figure 3:
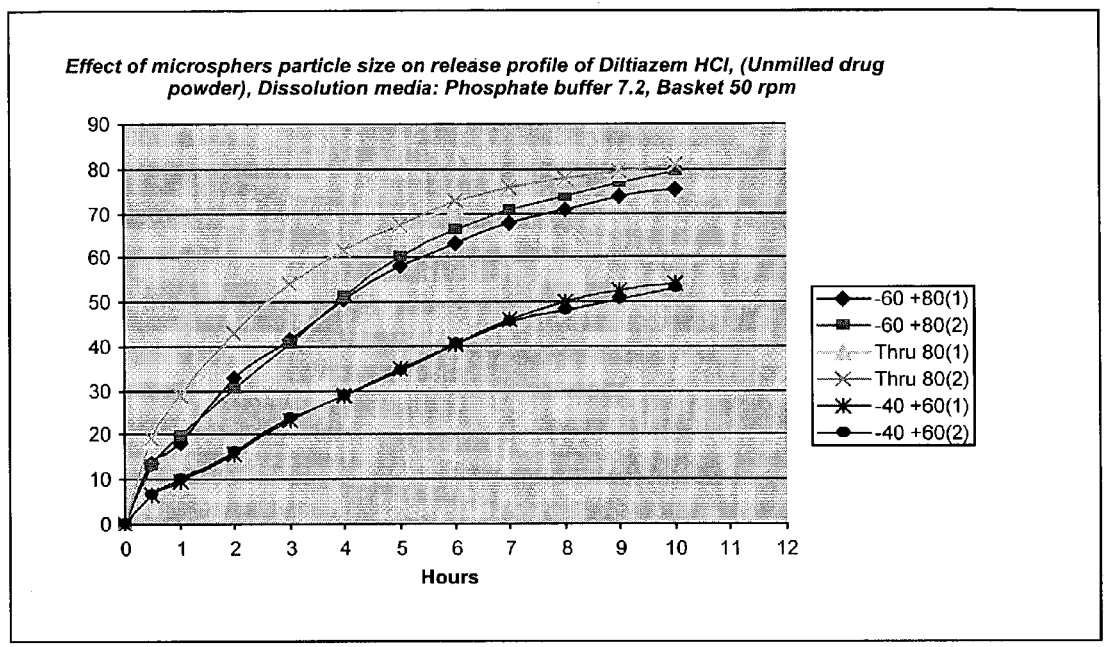
FIG. 3 is a plot of the percent release of various fractions of the microspheres prepared in accordance with Example 7 versus time.

The microcapsule prepared according to Example 7 is capable of releasing its core diltiazem by aqueous infiltration and exhibits a zero order release profile when introduced into an aqueous environment. The release of diltiazem (−20+40 mesh fraction) occurs at a constant rate for about 24 hours of stirring in a dissolution basket at 50 rpm at 37 degrees C. in accordance with the USP 24 procedure Test 5 (as modified, 900 ml of 0.05M phosphate buffer, pH 7.2). The percent release of various fractions of the microspheres prepared in accordance with Example 7 versus time data is presented in FIG. 3.

Comparative Example 8

Homogenizer Prepared Propranolol HCl Composition 525 g of milled propranolol HCl (<10 micron particle size) is mixed into a melt of 975 g of Dritex C, a commercially available polymorphic wax. The flowable pre-mixture is then homogenized in a Silverson homogenizer (Lab scale L4RTA) for five minutes and then the homogenized mixture is sprayed through a Nordson hot melt applicator maintained at 77 degrees C., driven by an electronic gear pump (Nordson 3700 series, speed setting=50%), aspirator pressure of 10 psi, needle set at 1.5 turn open from closed, into a chilled area. The propranolol HCl comprises 35% by weight of the microcapsule composition.

Figure 4:
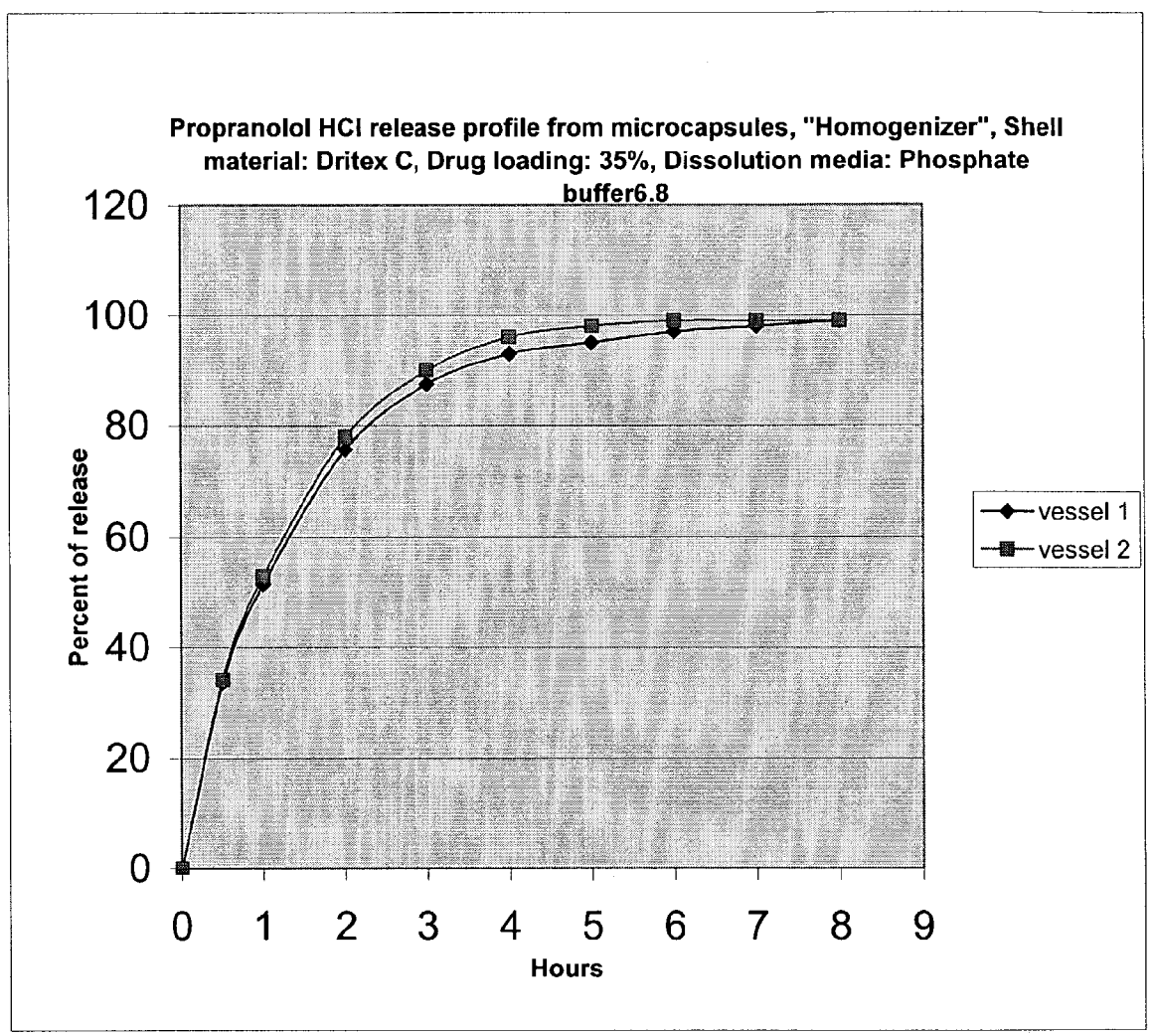
FIG. 4 is a plot of the per cent release versus time of a comparative composition.

The microcapsule prepared according to Comparative Example 8 releases 90% of its core propranolol in about 3 hours when introduced into an aqueous environment in a dissolution basket at 50 rpm at 37 degrees C. in accordance with the USP procedure Test 2 (as modified, 900 ml of 0.05M phosphate buffer, pH 6.8). The percent release versus time data is presented in FIG. 4.

Example 9

Zero Order Release Theophylline Composition 525 g of milled theophylline is mixed into a melt of a 50:50 mixture of 488 g of cetyl alcohol and 488 g of Dritex C. The flowable pre-mixture is then subjected to a pressure-force by passing it twice through a hydraulic piston driven pump, the "Beta" machine described in U.S. Pat. No. 5,209,879, set at 90 psi (Beta chamber configuration=entrance nozzle consisting of 4 holes (0.02 in ID), a chamber volume formed of spacers with a length of about 0.04 in and a diameter of about 0.25 in, and an exit nozzle consisting of four holes (0.02 in ID)). The pressure-treated mixture is sprayed through a Nordson hot melt applicator maintained at 77 degrees C. driven by an electronic gear pump Nordson 3700 series, speed setting=20–30%), aspirator pressure of 10 psi needle set at 1.5 turn open from closed, into a chilled area. The theophylline comprises 35% by weight of the microcapsule composition.

Figure 5:
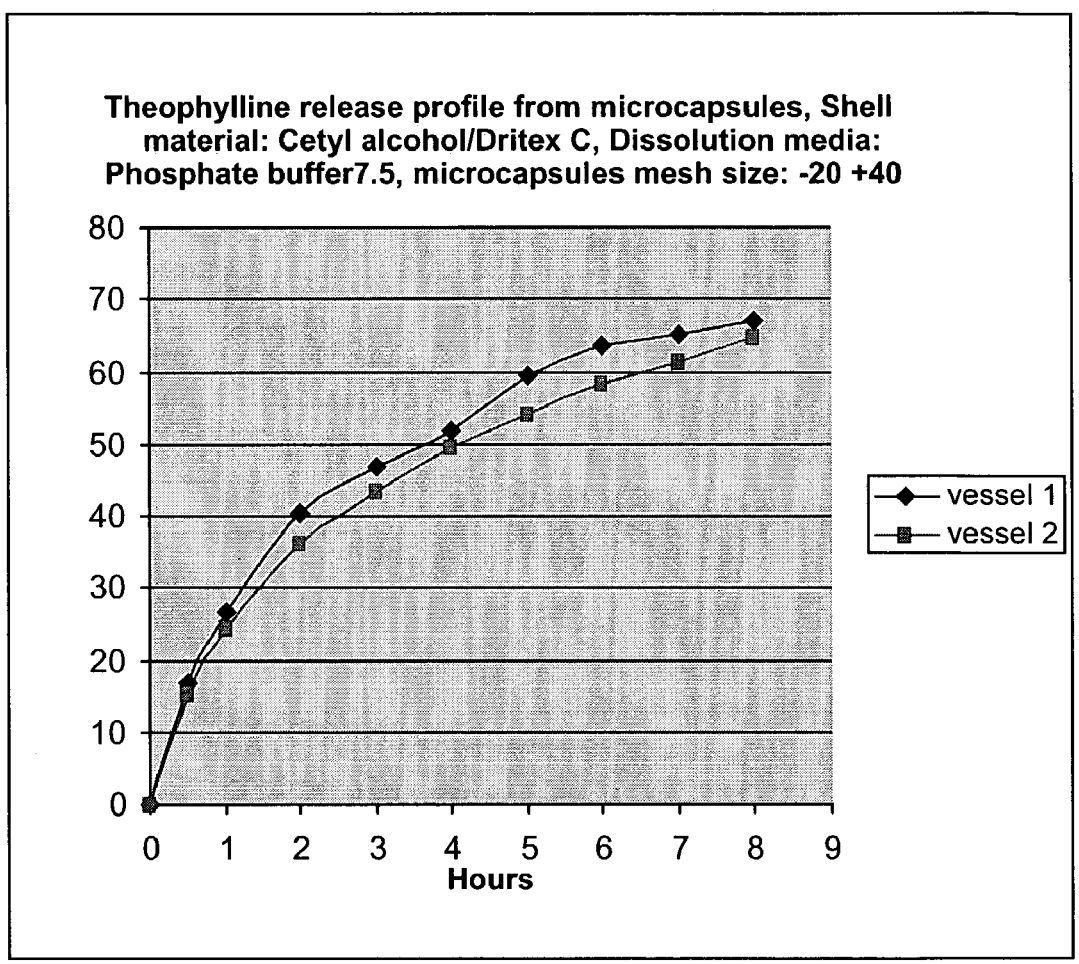
FIG. 5 is a plot of the release of theophylline composition of the present invention versus time.

The microcapsule prepared according to Example 9 is capable of releasing its core theophylline by aqueous infiltration and exhibits a zero order release profile when introduced into an aqueous environment. The release of theophylline (−20+40 mesh fraction) occurs at a constant rate for at least about 8 hours of stirring in a dissolution basket at 50 rpm at 37 degrees C. in accordance with the USP 24 procedure Test 8 (as modified, 900 ml 0.05M phosphate buffer, pH 7.5). The percent release versus time data is presented in FIG. 5.

Example 10

Microcapsule Size vs. Release Profiles

Figure 6:
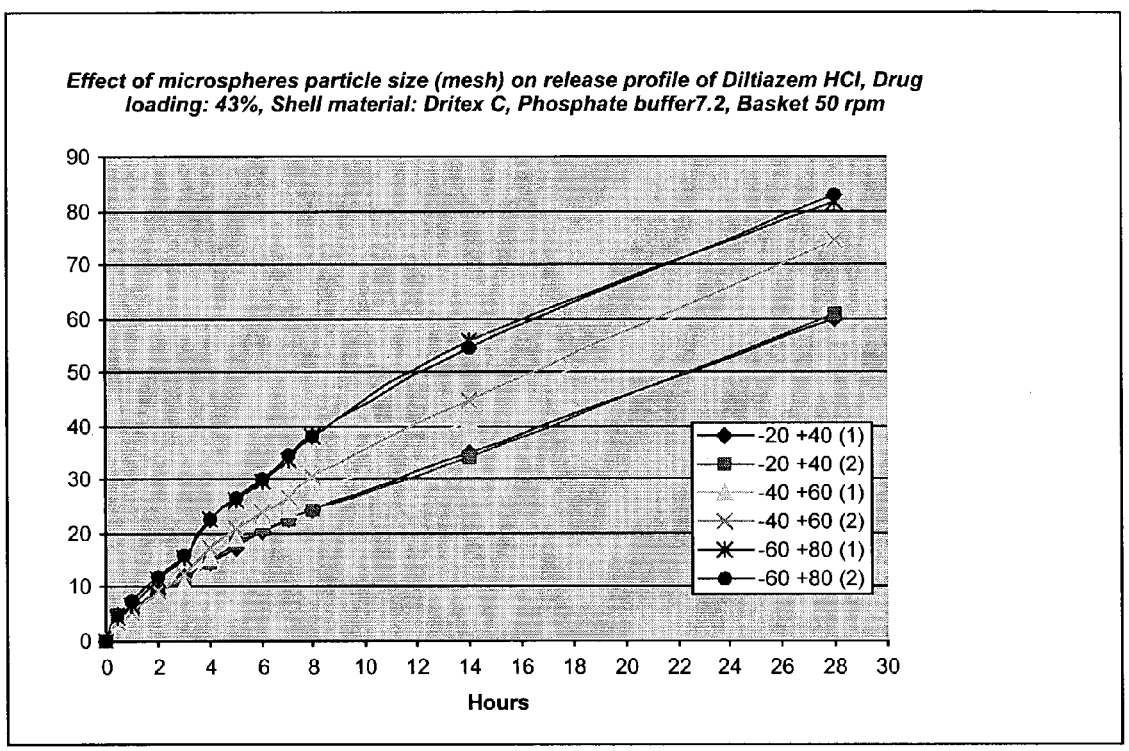
FIG. 6 is a plot of the effect of microcapsule particle size on the release profile.

The effect of microcapsule particle size on the release profile is shown in FIG. 6. The diltiazem HCl microcapsules tested in FIG. 6 were prepared in accordance with the procedure described in Example 7 (except the motor speed as set at 50%) and contains 43% by weight of diltiazem HCl in a shell consisting of Dritex C. The dissolution test is conducted in accordance with USP procedure Test 5 (for longer than 24 hours) (as modified, 900 ml 0.05M phosphate buffer at pH 7.2) at 37 degrees C. and a dissolution basket speed of 50 rpm.

The microcapsules were sieved into six fractions and each fraction subjected to the dissolution test conditions. It is clear that the particle size of the microcapsule influences only the rate at which the core material is released, and not the linearity of that release. The larger the microcapsule is, the slower the core material is released from the microcapsule.

The foregoing examples are exemplary of the methods and variety of melting ranges and zero-order release time ranges of the microcapsules of the present invention.

We claim:

1. A process for the manufacture of a water insoluble microsphere comprising a core material and a water insoluble shell material comprising:
   a. subjecting a flowable mixture of core material and a first amount of water insoluble shell material comprising a meltable polymer to a flowable pressure force to form a pressure-treated mixture; and
   b. spraying said flowable pressure-treated mixture into a chilling zone to form the solidified water insoluble microsphere.

2. A process according to claim 1 wherein said core material comprises solid particles.

3. A process according to claim 2 wherein said solid core particles are substantially spherical and have a mean particle size of from about 10 to about 50 microns.

4. A process according to claim 1 wherein said flowable mixture is maintained at a temperature above the solidification temperature of said shell material.

5. A process according to claim 4 wherein said mixture is maintained below the melting temperature of said shell material.

6. A process according to claim 5 wherein said shell material exhibits a melting curve where melting begins at T1 and is substantially complete at T2, and exhibits a cooling curve where solidification begins at T3 and is substantially complete at T4, wherein T3 is less than T1.

7. A process according to claim 6 wherein the difference between T1 and T2 is determined by the ratio of components comprising said shell material.

8. A process according to claim 1 wherein said composition is contacted with a second amount of a water insoluble shell material.

9. A process according to claim 8 wherein said composition is spray coated with a said second amount of shell material.

10. A process according to claim 9 wherein said second amount of shell material is from about 5 to about 30 percent by weight of the amount of shell material used to form said solidified composition.

11. A process according to claim 10 wherein said second amount of shell material is about 10 percent by weight of said first amount of shell material.

12. A process according to claim 9 wherein said first and second amounts of shell material comprise the same shell material.

13. A process according to claim 1 wherein said pressure force is applied for less than a second at a pressure of from about 2,000 psi to about 20,000 psi.

14. A process according to claim 1 wherein said pressure force is applied to said mixture which is passed through a chamber that subjects said mixture to cavitation and/or shear forces.

15. A process according to claim 6 wherein the melting point of said shell composition starts at about 106 degrees F. and is substantially complete at about 135 degrees F.

* * * * *